(12) United States Patent
Szeto

(10) Patent No.: US 11,101,038 B2
(45) Date of Patent: Aug. 24, 2021

(54) SYSTEMS AND METHODS FOR RESPONSE PREDICTION TO CHEMOTHERAPY IN HIGH GRADE BLADDER CANCER

(71) Applicant: NANTOMICS, LLC, Culver City, CA (US)

(72) Inventor: Christopher Szeto, Culver City, CA (US)

(73) Assignee: NantOmics, LLC, Culver City, CA (US)

( * ) Notice: Subject to any disclaimer, the term of this patent is extended or adjusted under 35 U.S.C. 154(b) by 861 days.

(21) Appl. No.: 15/543,418

(22) PCT Filed: Jan. 19, 2016

(86) PCT No.: PCT/US2016/013959
§ 371 (c)(1),
(2) Date: Jul. 13, 2017

(87) PCT Pub. No.: WO2016/118527
PCT Pub. Date: Jul. 28, 2016

(65) Prior Publication Data
US 2018/0004905 A1 Jan. 4, 2018

Related U.S. Application Data

(60) Provisional application No. 62/127,546, filed on Mar. 3, 2015, provisional application No. 62/105,697, filed on Jan. 20, 2015.

(51) Int. Cl.
*G16H 50/20* (2018.01)
*C12Q 1/6886* (2018.01)
(Continued)

(52) U.S. Cl.
CPC ........... *G16H 50/20* (2018.01); *C12Q 1/6886* (2013.01); *G16B 20/00* (2019.02); *G16B 40/00* (2019.02);
(Continued)

(58) Field of Classification Search
None
See application file for complete search history.

(56) References Cited

U.S. PATENT DOCUMENTS 7,899,764 B2    3/2011  Martin et al.
8,386,401 B2    2/2013  Virkar et al.
(Continued)

FOREIGN PATENT DOCUMENTS

AU    2016226162 B2    11/2017
AU    2018200276 A1     2/2018
(Continued)

OTHER PUBLICATIONS

Smith, S.C. et al., "A 20-gene model for molecular nodal staging of bladder cancer: development and prospective assessment," The Lancet Oncology vol. 12, No. 2 (2011) pp. 137-143, plus the web appendix supplementary material, 12 pp. (Year: 2011).*

(Continued)

*Primary Examiner* — Brian M Smith
(74) *Attorney, Agent, or Firm* — Martin Fessenmaier; Umberg Zipser LLP

(57) ABSTRACT

Contemplated systems and methods allow for prediction of chemotherapy outcome for patients diagnosed with high-grade bladder cancer. In particularly preferred aspects, the prediction is performed using a model based on machine learning wherein the model has a minimum predetermined accuracy gain and wherein a thusly identified model provides the identity and weight factors for omics data used in the outcome prediction.

9 Claims, 2 Drawing Sheets

(51) Int. Cl.
*G16B 20/00* (2019.01)
*G16B 40/00* (2019.01)
*G16H 50/50* (2018.01)
*G06N 20/20* (2019.01)
*G16B 40/20* (2019.01)
*G16B 20/20* (2019.01)

(52) U.S. Cl.
CPC ............ *G16B 40/20* (2019.02); *G16H 50/50* (2018.01); *C12Q 2600/106* (2013.01); *G06N 20/20* (2019.01); *G16B 20/20* (2019.02)

(56) References Cited

U.S. PATENT DOCUMENTS

| | | | |
|---|---|---|---|
| 8,484,225 | B1 | 7/2013 | Datta et al. |
| 2004/0193019 | A1 | 9/2004 | Wei |
| 2005/0210015 | A1 | 9/2005 | Zhou et al. |
| 2006/0173663 | A1 | 8/2006 | Langheier et al. |
| 2006/0195266 | A1 | 8/2006 | Yeatman |
| 2007/0128636 | A1 | 6/2007 | Baker et al. |
| 2008/0228753 | A1 | 9/2008 | Kenedy et al. |
| 2009/0319244 | A1 | 12/2009 | West et al. |
| 2011/0262921 | A1* | 10/2011 | Sabichi ............ G01N 33/57407 435/6.12 |
| 2012/0010866 | A1 | 1/2012 | Ramnarayan |
| 2012/0041683 | A1 | 2/2012 | Vaske et al. |
| 2012/0059670 | A1 | 3/2012 | Sanborn et al. |
| 2012/0066001 | A1 | 3/2012 | Sanborn et al. |
| 2012/0158391 | A1 | 6/2012 | Vaske et al. |
| 2012/0231959 | A1 | 9/2012 | Elton et al. |
| 2013/0085773 | A1 | 4/2013 | Yao et al. |
| 2013/0304484 | A1 | 11/2013 | Martinez et al. |
| 2014/0080731 | A1 | 3/2014 | Davicioni et al. |
| 2014/0143188 | A1 | 5/2014 | Mackey et al. |
| 2014/0193927 | A1 | 7/2014 | Schroder et al. |
| 2014/0199273 | A1 | 7/2014 | Cesano et al. |
| 2014/0279754 | A1 | 9/2014 | Barsoum et al. |
| 2016/0333421 | A1* | 11/2016 | Boutros ................. G16B 20/00 |

FOREIGN PATENT DOCUMENTS

| | | |
|---|---|---|
| AU | 2016209478 B2 | 3/2019 |
| AU | 2018200276 B2 | 5/2019 |
| CA | 2 974 199 A1 | 7/2016 |
| CA | 2 978 708 A1 | 9/2016 |
| CN | 107548498 A | 1/2018 |
| CN | 107980162 A | 5/2018 |
| EP | 2 669 682 A1 | 12/2013 |
| EP | 3248127 A1 | 11/2017 |
| JP | 2005-521138 A | 7/2005 |
| JP | 2013000067 A | 1/2013 |
| JP | 2015-502740 A | 1/2015 |
| JP | 2018-507470 A | 3/2018 |
| JP | 2018-513461 A | 5/2018 |
| JP | 2018-173969 A | 11/2018 |
| KR | 10-2018-0008403 A | 1/2018 |
| KR | 10-2018-0010176 A | 1/2018 |
| KR | 10-2019-0047108 A | 5/2019 |
| WO | 03/079286 A1 | 9/2003 |
| WO | 2005008213 A2 | 1/2005 |
| WO | 2005/008213 A3 | 3/2005 |
| WO | 2005/100606 A2 | 10/2005 |
| WO | 2008067551 A2 | 6/2008 |
| WO | 2009/073478 A2 | 6/2009 |
| WO | 2011/139345 A2 | 11/2011 |
| WO | 2012009382 | 1/2012 |
| WO | 2012009382 A2 | 1/2012 |
| WO | 2012009382 A3 | 1/2012 |
| WO | 2012030840 A2 | 3/2012 |
| WO | 2012009382 A3 | 4/2012 |
| WO | 2012/170715 A1 | 12/2012 |
| WO | 2013/059732 A1 | 4/2013 |
| WO | 2013/062505 A1 | 5/2013 |
| WO | 2013090620 | 6/2013 |
| WO | 2013090620 A1 | 6/2013 |
| WO | 2013144362 A1 | 10/2013 |
| WO | 2014043803 A1 | 3/2014 |
| WO | 2014/059036 A1 | 4/2014 |
| WO | 2014/193982 A1 | 12/2014 |
| WO | 2016/118527 A1 | 7/2016 |
| WO | 2016/141214 A1 | 9/2016 |

OTHER PUBLICATIONS

Als, A. B. et al., "Emmprin ans Survivin predict response and survival following Cisplatin-containing chemotherapy in patients with advanced bladder cancer," Clinical Cancer Research, vol. 13, No. 15 (2007) pp. 4407-4414. (Year: 2007).*

Gustafsson, M. et al., "Gene expression prediction by soft integration and the elastic net—best performance of the DREAM3 gene expression challenge," PLoS ONE, vol. 5, Issue 2 (2010) 8 pp. (Year: 2010).*

Derisi, J. et al., "Use of a cDNA microarray to anayse gene expression patterns in human cancer," Nature Genetics, vol. 14 (1996) pp. 457-(Year: 1996).*

Todorovski, L. et al. "Predictive performance of weighted relative accuracy," PKDD 2000, LNAI 1910 (2000) pp. 255-264. (Year: 2000).*

Kanojia, D. et al., "Sperm associated antigen 9 plays an important role in bladder transitional cell carcinoma," PLoS ONE vol. 8, No. 12 (2013) 12 pp. (Year: 2013).*

Korean Patent Office, Notice to File a Response, dated Feb. 28, 2019.

International Search Report and Written Opinion received for PCT Application Serial No. PCT/US2016/013959 dated May 4, 2016, 23 pages.

First Examination Report received for Australian Patent Application Serial No. 2016366744 dated Mar. 20, 2019, 09 pages.

International Preliminary Report on Patentability received for PCT Application Serial No. PCT/US2016/013959 dated Jun. 14, 2017, 35 pages.

Examination Report received for Australian Patent Application Serial No. 2016209478 dated Oct. 12, 2018, 03 pages.

Extended European Search Report received for European Patent Application Serial No. 16740607.3 dated Jul. 10, 2018, 4 page.

First Office Action received for Japanese Patent Application Serial No. 2017537902 dated Sep. 10, 2019, 08 pages (Including English Translation).

Notification of Reason of Refusal received for Korean Patent Application Serial No. 1020177023267 dated Sep. 30, 2019, 17 pages. (Including English Translation).

Kulkarni et al., "TLE3 as a candidate biomarker of response to taxane therapy", Breast Cancer Research, 2009, vol. 11, No. 2, pp. 1-10.

Jaremko et al., "Polymorphism of the DNA repair enzyme XRCC1 is associated with treatment prediction in anthracycline and cyclophosphamide/methorexate/5-fluorouracil-based chemotherapy of patients with primary invasive breast cancer", Pharmacogenetics and Genomics, 2007, vol. 17, No. 7, pp. 529-538.

Tengstrom et al. "XRCC1 rs25487 Polymorphism Predicts the Survival of Patients After Postoperative Radiotherapy and Adjuvant Chemotherapy for Breast Cancer", Anticancer Research, 2014, vol. 34, No. 6, pp. 3031-3038.

Notice of Acceptance received for Australian Patent Application Serial No. 2016209478, dated Feb. 25, 2019, 3 pages.

Bayer et al., "Prediction Errors in Learning Drug Response from Gene Expression Data-influence of Labeling, Sample Size, and Machine Learning Algorithm", PLoS ONE 8(7): vol. 8, Issue 7, e70294, Jul. 23, 2013.

Cornero et al., "Design of a multi-signature ensemble classifier predicting neuroblastoma patients' outcome", Eighth Annual Meeting of the Italian Society of Bioinformatics (BITS) Pisa, Italy. Jun. 20-22, 2011, pp. 1-12.

Escalante et al., "Ensemble Particle Swarm Model Selection", National Institute of Astrophysics, Tonantzintla, Puebla, Mexico.

(56) References Cited

OTHER PUBLICATIONS

ISA/KR, International Search Report and Written Opinion, completed Jun. 7, 2016 for PCT Application No. PCT/US2016/020742, 8 pages.
Shouval et al, Application of machine learning algorithms for clinical predictive modeling: a data-mining approach in SCT, Bone Marrow Transplantation (2014), vol. 49, pp. 332-337.
Israel Patent Office, Office Action, dated Mar. 19, 2019.
Examination Report received for Australian Patent Application Serial No. 2019203295 dated Mar. 23, 2020, 03 pages.
First Office Action received for Chinese Patent Application Serial No. 201680008725.2 dated Apr. 3, 2020, 15 pages (including English Translation).
Grant of Patent received in Korean Patent Application Serial No. 1020177023267 dated Apr. 7, 2020, 2 pages (including English Translation).
Decision to Grant received for Japanese Patent Application Serial No. 2017537902 dated Jun. 9, 2020, 5 pages (Including English translation).
Office Action Received for Japanese Patent Application Serial No. 2018-112693 dated Aug. 29, 2019, 3 Pages (Including English translation).
Examiner's Report issued for Canadian Application No. 2,978,708, dated Sep. 30, 2019, 4 pages.
First Examination Report received for Australian Patent Application Serial No. 2016226162 dated Oct. 25, 2017, 5 Pages.
Notice of acceptance received for Australian Patent Application Serial No. 2016226162 dated Nov. 10, 2017, 3 Pages.
First Examination Report received for Australian Patent Application Serial No. 2018200276 dated Jan. 11, 2019, 2 Pages.
Notice of acceptance received for Australian Patent Application Serial No. 2018200276 dated Apr. 10, 2019, 3 Pages.
Office Action received for Canadian Patent Application Serial No. 2978708 dated Dec. 14, 2017, 7 pages.
Office Action received for Canadian Patent Application Serial No. 2978708 dated Jun. 22, 2018, 3 pages.
Office Action received for Canadian Patent Application Serial No. 2978708 dated Jan. 30, 2019, 4 pages.
Extended European Search Report received in European Patent Application Serial No. 16759516.4 dated Nov. 22, 2018, 10 pages.
Decision to Grant received for Japanese Patent Application Serial No. 2017546211 dated May 15, 2018, 5 pages (Including English translation).
International Preliminary Report on Patentability received in PCT Application Serial No. PCT/US2016/020742 dated Sep. 14, 2017, 7 pages.
Office Action received in Korean Patent Application Serial No. 1020177027662 dated Oct. 18, 2018, 7 pages (Including English translation).
Notice of Allowance received in Canadian Patent Application Serial No. 2978708 dated Feb. 14, 2020, 1 page.
Office Action received in Israel Patent Application Serial No. 258482 dated Nov. 25, 2018, 5 pages (including English Translation).
Office Action received in Israel Patent Application Serial No. 254279 dated Jan. 17, 2018, 5 pages (including English Translation).
Office Action received in Israel Patent Application Serial No. 258482 dated Jan. 13, 2020, 5 pages (including English Translation).
Non Final Office Action received for U.S. Appl. No. 15/555,290 dated May 29, 2020, 53 pages.
Leung et al, Machine Learning in Genomic Medicine: A Review of Computational Problems and Data Sets Proceedings of the IEEE, vol. 104, No. 1, Jan. 2016.
Holzinger et al, Interactive Knowledge Discovery and Data Mining in Biomedical Informatics State-of-the-Art and Future Challenges Springer 2014 ISSN 0302-9743.
Notice of Defects received for Israeli Patent Application Serial No. 253550 dated Jan. 16, 2020, 3 pages (including English Translation).

* cited by examiner

SYSTEMS AND METHODS FOR RESPONSE PREDICTION TO CHEMOTHERAPY IN HIGH GRADE BLADDER CANCER

This application claims priority to US provisional application with the Ser. No. 62/105,697, which was filed 20 Jan. 2015, and US provisional application with the Ser. No. 62/127,546, which was filed 3 Mar. 2015, both of which are incorporated by reference herein.

FIELD OF THE INVENTION

The field of the invention is in silico systems and methods for prediction of treatment outcome for chemotherapy in bladder cancer.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Selection of pharmaceutical treatment options for cancer has historically been limited to empirical data and histological findings to so match a drug to a particular cancer type. More recently, advances in molecular medicine have allowed a more personalized approach in the choice of chemotherapy, taking into account presence or absence of specific receptors on a cell, mutational status of signaling molecules, etc. While such improvements have translated at least in some cases to increased survival time, response to a chemotherapeutic drug is in all or almost all cases not entirely predictable. Moreover, once a patient is committed to a specific treatment regimen, changes in treatment protocol are often not advised and/or poorly tolerated by the patient.

To help predict likely treatment outcome for pharmaceutical interventions, various computational systems and methods have been developed. Most notably, WO 2014/193982 describes systems and methods in which pathway elements (corresponding to cellular in vivo features) of a pathway model are modified in silico to simulate treatment of a cell with a drug. The modified model can then be used to help predict the effect of the drug on one or more pathways, and indirectly predict the effect of the drug on a diseased tissue. While such system has provided remarkable predictive power in certain circumstances, such system was based on cell culture data and as such did not fully reflect in vivo environments. Moreover, simulation of the treatment was performed using a single model that was rooted in measured and assumed attributes and therefore relied on specific assumptions genuine to the model. The described approach fails to provide insight into mitigating risks associated with the specific assumptions of model.

To accommodate large quantities of data from complex in vivo systems, computer-based machine learning technologies have been developed that can ingest large data sets that exceed the capacity of human beings to assimilate. In general, machine learning algorithms are often configured to identify patterns in training data sets so that the algorithms "learn" or become "trained" how to predict possible outcomes when presented with new input data. Notably, there are numerous types of machine learning algorithms, each having their own specific underlying mode of analysis (e.g., support vector machines, Bayesian statistics, Random Forests, etc.), and with that inherent bias. An example for such analysis is presented in US2004/0193019 to Wei in which discriminant analysis-based pattern recognition is used to generate a prediction model that correlates biological profile information with treatment outcome information. The so formed prediction model is then used to rank possible responses to treatment. Wei simply builds prediction outcome models to make an assessment of likely outcome based patient-specific profile information. Unfortunately, not all algorithms will be suitable for predictive analysis of drug treatment as each algorithm has built in assumptions that might not be valid for the specific disease and/or drug treatment. Furthermore, models that are maximized for a particular prediction will not necessarily provide the best accuracy as compared to a random event and/or other model.

To address such difficulties, US 2014/0199273 to Cesano et al. discusses selection of specific models/statistical methods that are suitable for prediction or prognosis in a healthcare setting. While Cesano discusses selection of suitable models, these models, once selected still suffer from the same difficulties of inherent bias.

Thus, even though various system and methods of treatment prediction are known in the art, all or almost all of them suffer from various disadvantages. Therefore, there is still a need for systems and methods that help to more accurately predict drug treatment response of a cancer patient to an intended chemotherapy before commencing treatment.

SUMMARY OF THE INVENTION

The inventor has discovered that a predictive model for treatment outcome for high-grade bladder cancer can be derived from a collection of models that were prepared using various machine learning algorithms trained on previously known high-grade bladder cancer omics information that was associated with treatment outcome. Most preferably, prediction accuracy is improved by identification of a model with high accuracy gain and selection of omics parameters and associated weighting from the identified model.

In one aspect of the inventive subject matter, the inventor contemplates a method of predicting treatment outcome for a patient having high-grade bladder cancer. In preferred aspects contemplated methods include a step of obtaining a plurality of omics data from the patient, and a further step of (a) using an accuracy gain metric to select at least a single model for prediction of the treatment outcome of high grade bladder cancer treatment or (b) selecting at least a single model on the basis of a previously determined accuracy gain metric for prediction of the treatment outcome of high grade bladder cancer treatment. Models may be selected from among a large number, for example, from among at least 10 trained models or from among at least 100 trained models or even more. In yet another step, an analysis engine then calculates a prediction outcome (e.g., complete response to treatment, partial response to treatment, stable non-response to treatment, and progressive non-response to treatment) using the single model and the plurality of omics data from the patient.

Most typically, the omics data include whole genome differential objects, exome differential objects, SNP data, copy number data, RNA transcription data, protein expression data, and/or protein activity data, and it is further preferred that the accuracy gain metric may be an accuracy gain, an accuracy gain distribution, an area under curve metric, an $R^2$ metric, a p-value metric, a silhouette coefficient, and/or a confusion matrix. While not limiting the inventive subject matter, it is also contemplated that the accuracy gain metric of the single model is within the upper quartile of all models, or within the top 5% of all models, or wherein the accuracy gain metric of the single model exceeds all other models.

In further contemplated aspects, the single model may be generated using a machine learning algorithm that uses a classifier selected form the group consisting of NMFpredictor (linear), SVMlight (linear), SVMlight first order polynomial kernel (degree-d polynomial), SVMlight second order polynomial kernel (degree-d polynomial), Waikato Environment for Knowledge Analysis (WEKA) SMO (linear), WEKA j48 trees (trees-based), WEKA hyper pipes (distribution-based), WEKA random forests (trees-based), WEKA naive Bayes (probabilistic/bayes), WEKA JRip (rules-based), glmnet lasso (sparse linear), glmnet ridge regression (sparse linear), and glmnet elastic nets (sparse linear).

Most preferably, the step of calculating comprises a step of selecting features of the single model having minimum absolute predetermined weights (e.g., within the top quartile of all weights in the single model). While numerous features may be suitable, it is contemplated that the step of calculating uses at least 10 distinct selected features in the single model. In particularly preferred methods for high-grade bladder cancer, the features of the single model are RNA transcription values for genes selected from the group consisting of PCDHGA4, PCDHGB1, HSP90AB2P, SPAG9, DDI2, TOP1P2, AGAP1, BBS9, FNIP2, LOC647121, NFIC, TGFBRAP1, EPRS, C9orf129, SARS, RBM28, NACC2, GTPBP5, PRKAR2A, CDK8, FAM24B, CRK, RAB2A, SMAD2, ELP2, WWP1, KIF5B, RPL39, PSEN1, SURF4, TTC35, TOM1, TES, VWA1, GOLGA2, ARHGAP21, FLJ37201, KIAA1429, AZIN1, SCAMP2, H1F0, PYCR1, SEC24D, FLNB, PATL1, HDLBP, RRBP1, OXR1, GLB1, NPEPPS, KIF1C, DDB1, and GSN. Moreover, it is contemplated that the RNA transcription values for the genes are calculated with respective factors, that the respective factors are weighted, and that (using absolute values), the weights are in the order of PCDHGA4, PCDHGB1, HSP90AB2P, SPAG9, DDI2, TOP1P2, AGAP1, BBS9, FNIP2, LOC647121, NFIC, TGFBRAP1, EPRS, C9orf129, SARS, RBM28, NACC2, GTPBP5, PRKAR2A, CDK8, FAM24B, CRK, RAB2A, SMAD2, ELP2, WWP1, KIF5B, RPL39, PSEN1, SURF4, TTC35, TOM1, TES, VWA1, GOLGA2, ARHGAP21, FLJ37201, KIAA1429, AZIN1, SCAMP2, H1F0, PYCR1, SEC24D, FLNB, PATL1, HDLBP, RRBP1, OXR1, GLB1, NPEPPS, KIF1C, DDB1, and GSN.

Viewed from a different perspective, the inventors therefore also contemplate a method of predicting treatment outcome for a patient having high-grade bladder cancer. Such methods will preferably include a step of obtaining plurality of RNA transcription data of the patient, and a further step of calculating, by an analysis engine and using the plurality of RNA transcription data of the patient, a treatment outcome score using a model. Most typically, the model uses RNA transcription values for genes selected from the group consisting of PCDHGA4, PCDHGB1, HSP90AB2P, SPAG9, DDI2, TOP1P2, AGAP1, BBS9, FNIP2, LOC647121, NFIC, TGFBRAP1, EPRS, C9orf129, SARS, RBM28, NACC2, GTPBP5, PRKAR2A, CDK8, FAM24B, CRK, RAB2A, SMAD2, ELP2, WWP1, KIF5B, RPL39, PSEN1, SURF4, TTC35, TOM1, TES, VWA1, GOLGA2, ARHGAP21, FLJ37201, KIAA1429, AZIN1, SCAMP2, H1F0, PYCR1, SEC24D, FLNB, PATL1, HDLBP, RRBP1, OXR1, GLB1, NPEPPS, KIF1C, DDB1, and GSN.

Most preferably, the plurality of RNA transcription data are obtained from polyA RNA, and/or the treatment outcome score is indicative of a complete response to treatment, a partial response to treatment, a stable non-response to treatment, or a progressive non-response to treatment. As already noted above it is contemplated that the model was generated using a machine learning algorithm that uses a classifier selected form the group consisting of NMFpredictor (linear), SVMlight (linear), SVMlight first order polynomial kernel (degree-d polynomial), SVMlight second order polynomial kernel (degree-d polynomial), WEKA SMO (linear), WEKA j48 trees (trees-based), WEKA hyper pipes (distribution-based), WEKA random forests (trees-based), WEKA naive Bayes (probabilistic/bayes), WEKA JRip (rules-based), glmnet lasso (sparse linear), glmnet ridge regression (sparse linear), and glmnet elastic nets (sparse linear), and/or that the RNA transcription values for the genes are calculated with respective factors, and wherein the respective factors are weighted, using absolute values, in the order of PCDHGA4, PCDHGB1, HSP90AB2P, SPAG9, DDI2, TOP1P2, AGAP1, BBS9, FNIP2, LOC647121, NFIC, TGFBRAP1, EPRS, C9orf129, SARS, RBM28, NACC2, GTPBP5, PRKAR2A, CDK8, FAM24B, CRK, RAB2A, SMAD2, ELP2, WWP1, KIF5B, RPL39, PSEN1, SURF4, TTC35, TOM1, TES, VWA1, GOLGA2, ARHGAP21, FLJ37201, KIAA1429, AZIN1, SCAMP2, H1F0, PYCR1, SEC24D, FLNB, PATL1, HDLBP, RRBP1, OXR1, GLB1, NPEPPS, KIF1C, DDB1, and GSN.

Consequently, the inventors also contemplate a method of predicting treatment outcome for a patient having high-grade bladder cancer. Especially preferred such methods include a step of obtaining plurality of RNA transcription data of the patient, wherein the RNA transcription values are values for at least two genes selected from the group consisting of PCDHGA4, PCDHGB1, HSP90AB2P, SPAG9, DDI2, TOP1P2, AGAP1, BBS9, FNIP2, LOC647121, NFIC, TGFBRAP1, EPRS, C9orf129, SARS, RBM28, NACC2, GTPBP5, PRKAR2A, CDK8, FAM24B, CRK, RAB2A, SMAD2, ELP2, WWP1, KIF5B, RPL39, PSEN1, SURF4, TTC35, TOM1, TES, VWA1, GOLGA2, ARHGAP21, FLJ37201, KIAA1429, AZIN1, SCAMP2, H1F0, PYCR1, SEC24D, FLNB, PATL1, HDLBP, RRBP1, OXR1, GLB1, NPEPPS, KIF1C, DDB1, and GSN; and a further step of using the RNA transcription values in a model generated by a machine learning algorithm to so predict treatment outcome for the patient.

While not limiting to the inventive subject matter, it is typically preferred that the machine learning algorithm uses a classifier selected form the group consisting of NMFpredictor (linear), SVMlight (linear), SVMlight first order polynomial kernel (degree-d polynomial), SVMlight second order polynomial kernel (degree-d polynomial), WEKA SMO (linear), WEKA j48 trees (trees-based), WEKA hyper pipes (distribution-based), WEKA random forests (trees-based), WEKA naive Bayes (probabilistic/bayes), WEKA JRip (rules-based), glmnet lasso (sparse linear), glmnet ridge regression (sparse linear), and glmnet elastic nets (sparse linear). Moreover, it is contemplated that the RNA transcription values for the genes are calculated with respective factors, and that the respective factors are weighted, using absolute values, in the order of PCDHGA4, PCDHGB1, HSP90AB2P, SPAG9, DDI2, TOP1P2, AGAP1, BBS9, FNIP2, LOC647121, NFIC, TGFBRAP1, EPRS, C9orf129, SARS, RBM28, NACC2, GTPBP5, PRKAR2A, CDK8, FAM24B, CRK, RAB2A, SMAD2, ELP2, WWP1, KIF5B, RPL39, PSEN1, SURF4, TTC35, TOM1, TES, VWA1, GOLGA2, ARHGAP21, FLJ37201, KIAA1429, AZIN1, SCAMP2, H1F0, PYCR1, SEC24D, FLNB, PATL1, HDLBP, RRBP1, OXR1, GLB1, NPEPPS, KIF1C, DDB1, and GSN.

Thus, the inventors also contemplate use of RNA transcription values for prediction of the treatment outcome of high grade bladder cancer treatment, wherein the prediction uses a single model obtained from a machine learning algorithm, and wherein the RNA transcription values are for genes selected from the group consisting of PCDHGA4, PCDHGB1, HSP90AB2P, SPAG9, DDI2, TOP1P2, AGAP1, BBS9, FNIP2, LOC647121, NFIC, TGFBRAP1, EPRS, C9orf129, SARS, RBM28, NACC2, GTPBP5, PRKAR2A, CDK8, FAM24B, CRK, RAB2A, SMAD2, ELP2, WWP1, KIF5B, RPL39, PSEN1, SURF4, TTC35, TOM1, TES, VWA1, GOLGA2, ARHGAP21, FLJ37201, KIAA1429, AZIN1, SCAMP2, H1F0, PYCR1, SEC24D, FLNB, PATL1, HDLBP, RRBP1, OXR1, GLB1, NPEPPS, KIF1C, DDB1, and GSN. Typically, but not necessarily, the RNA transcription values for the genes are calculated with respective factors, and wherein the respective factors are weighted, using absolute values, in the order of PCDHGA4, PCDHGB1, HSP90AB2P, SPAG9, DDI2, TOP1P2, AGAP1, BBS9, FNIP2, LOC647121, NFIC, TGFBRAP1, EPRS, C9orf129, SARS, RBM28, NACC2, GTPBP5, PRKAR2A, CDK8, FAM24B, CRK, RAB2A, SMAD2, ELP2, WWP1, KIF5B, RPL39, PSEN1, SURF4, TTC35, TOM1, TES, VWA1, GOLGA2, ARHGAP21, FLJ37201, KIAA1429, AZIN1, SCAMP2, H1F0, PYCR1, SEC24D, FLNB, PATL1, HDLBP, RRBP1, OXR1, GLB1, NPEPPS, KIF1C, DDB1, and GSN.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
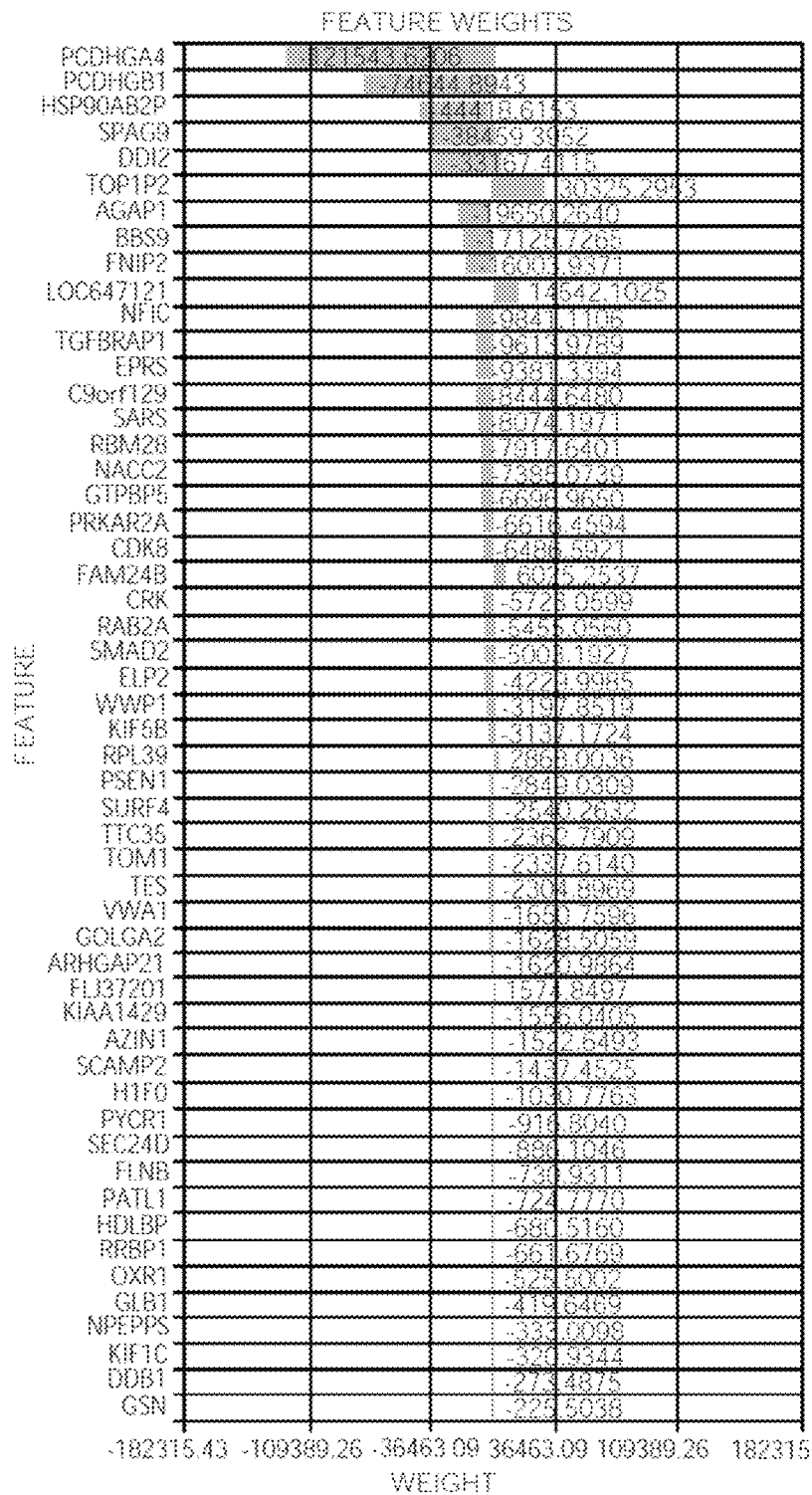
FIG. 1 is an exemplary table of features and feature weights derived from a model with high accuracy gain using TCGA high-grade bladder cancer data.

The inventive subject matter is directed to various computer systems and methods in which genomic information for a relatively large class of patients suffering from a particular neoplastic disease (e.g., bladder cancer) is subjected to a relatively large number of machine learning algorithms to so identify a corresponding large number of predictive models. The predictive models are then analyzed for accuracy gain, and the model(s) with the highest accuracy gain will then be used to identify relevant omics factors for the prediction.

Thus, it should be especially appreciated that contemplated systems and methods are neither based on prediction optimization of a singular model nor based on identification of best correlations of selected omics parameters with a treatment prediction. Instead, it should be recognized that contemplated systems and methods rely on the identification of omics parameters and associated weighting factors that are derived from one or more implementations of machine learning algorithms that result in trained models having a predetermined or minimum accuracy gain. Notably, the so identified omics parameters will typically have no statistically predictive power by themselves and as such would not be used in any omics based test system. However, where such identified omics parameters are used in the context of a trained model that has high accuracy gain, multiple omics parameters will provide a system with high predictive power, particularly when applied in the system using weighting factors associated with the trained model. Of course, it should also be appreciated that such model and omics parameters and weightings are unique to the particular training sets and/or type of outcome prediction, and that other diseases (e.g., lung cancer) and/or outcome predictions (e.g., survival time past 5 years) may lead to entirely different models, omics parameters, and weightings. Thus, the inventor is considered to have discovered weightings and/or trained models that have high predictive power associated with high-grade bladder cancer. In addition, treatment prediction can be validated from the a priori identified pathway(s) and/or pathway element(s), or identified pathways and/or pathway elements by in silico modulation using known pathway modeling system and methods to so help confirm treatment strategy predicted by the system.

It is therefore contemplated that the inventive subject matter is directed to various systems and methods in which genomic information and associated meta data for a relatively large class of patients suffering from a high-grade bladder cancer is subjected to multiple and distinct machine learning algorithms. In one preferred aspect of the inventive subject matter, RNA transcription values and associated meta data (e.g., treatment outcome) are subject to training and validation splitting in a preprocessing step that then provides the data to different machine-learning packages for analysis.

It should be noted that the focus of the disclosed inventive subject matter is to enable construction or configuration of a computing device(s) to operate on vast quantities of digital data, beyond the capabilities of a human. Although the digital data can represent machine-trained computer models of omics data and treatment outcomes, it should be appreciated that the digital data is a representation of one or more digital models of such real-world items, not the actual items. Rather, by properly configuring or programming the devices as disclosed herein, through the instantiation of such digital models in the memory of the computing devices, the computing devices are able to manage the digital data or models in a manner that would be beyond the capability of a human. Furthermore, the computing devices lack a priori capabilities without such configuration. In addition, it should be appreciated that the present inventive subject matter significantly improves/alleviates problems inherent to computational analysis of complex omics calculations.

Viewed from a different perspective, it should be appreciated that the present systems and methods in computer technology is being used to solve a problem inherent in computing models for omics data. Thus, without computers, the problem, and thus the present inventive subject matter, would not exist. More specifically, the disclosed approach results in one or more optimized trained models having greater accuracy gain than other trained models that are less capable, which results in less latency in generating predictive results based on patient data.

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions configure or otherwise program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network, circuit switched network, and/or cell switched network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions or operate on target data or data objects stored in the memory.

For example, in the analysis of high-grade bladder cancer, a large number of genomic data with respective meta data from patients diagnosed with high-grade bladder cancer were processed to create training data sets that were then fed into a collection of model templates (i.e., software implementations of machine learning algorithms). Using the data sets and machine learning systems, corresponding trained models were created that were subsequently analyzed (and ranked) for accuracy gain as further described below. From the model with the highest accuracy gain, omics parameters and weighting factors for each of the parameters were extracted and used as the predictive model.

More specifically, and using the above approach, the inventor investigated by analysis of publicly available data (here: TCGA BLCA data) which of the high-grade bladder cancer patients in the data would respond to chemotherapy, which could at least potentially eliminate surgery. In this dataset, 116 drug treatment courses were tracked in 50 patients. Of these 116 treatments, 111 were chemotherapy agents, including Adriamycin, Avastin, Carboplatin, Cisplatin, Docetaxel, Doxorubicin, Etopside, Gemcitabine, Ifosfamide, Methotrexate, Paclitaxel and Vinblastine (or equivalent brand names for these drugs). Of these 111 chemotherapy treatments 78 had 'treatment best response' recorded. If a patient had a chemotherapy agent with Complete or Partial Response recorded, they were considered a "chemotherapy responder". If they had Clinical Progressive or Stable disease, they were considered a "chemotherapy non-responder". A total of 33 patients had a chemotherapy response recorded (15 non-responders and 18 responders). All 33 patients were confirmed to be high-grade bladder cancer patients using further TCGA clinical information.

These data were used to generate 72 candidate predictive models of which patients with high grade tumors could respond to chemotherapy. Each model was trained using k-fold cross-validation by splitting the data set into training sets and validation sets. Twenty-four predictive models were calculated for each of the available data sets using prediction model templates available via scikit-learn (scikit-learn developers, online scikit-learn.org), using various classifiers, including linear classifiers, NMF-based classifiers, graphical-based classifiers, tree-based classifiers, Bayesian-based classifiers, and net-based classifiers, yielding 360 evaluation models. All of the so constructed evaluation models were then subjected to accuracy gain analysis to identify the model building process with the highest accuracy gain. In this example, accuracy gain was calculated by comparison of the correct prediction percentage using the validation data set against the percentage (frequency) of occurrence of the majority classifier (here: treatment is responsive). For example, where responsive treatment frequency is 60% in the known data set and where the model correctly predicts 85% of the treatment outcome as responsive, the accuracy gain is 25%. Notably, over all models constructed, the best model building process was 88% accurate in cross-validation testing folds (which was 33% better than majority) and used an elastic net classifier. The final fully-trained model that used the most accurate build process was selected from the 72 candidate models.

It should be appreciated that using such approach will rapidly generate a relatively large number of trained models. For example, where n algorithms are used with m types of input data sets using p fold cross validation, the overall number of trained models is n×m×p. All of the so constructed models were then subjected to accuracy gain analysis to identify the model with the highest accuracy gain. In this example, accuracy gain was calculated by comparison of the correct prediction percentage using the validation data set against the percentage (frequency) of occurrence of the majority classifier (here: treatment is responsive). For example, where responsive treatment frequency is 60% in the known data set and where the model correctly predicts 85% of the treatment outcome as responsive, the accuracy gain is 25%. Notably, over all models constructed, the best model was 88% accurate in cross-validation testing folds (which was 33% better than majority) and used an elastic net classifier.

In this context it must be appreciated that each type of model includes inherent biases or assumptions, which may influence how a resulting trained model would operate relative to other types of trained models, even when trained on identical data. Accordingly, different models will produce different predictions/accuracy gains when using the same training data set. Heretofore, in an attempt to improve prediction outcome, single machine learning algorithms were optimized to increase correct prediction on the same data set. However, due to inherent bias of the algorithms, such optimization will not necessarily increase accuracy (i.e., accurate prediction capability against 'coin flip') in predictability. Such bias can be overcome by training numerous diverse models with different underlying principles and classifiers on disease-specific data sets with associated metadata and by selecting from the so trained models those with desirable accuracy gain or robustness.

Once a desired model with high accuracy gain is selected, omic parameters with high relevance can then be selected from the model to produce a predictive model with improved accuracy of prediction. FIG. 1 exemplarily depicts a collection of genes encoding an RNA where the omics data from a patient are RNA transcription data (transcription strength). Here, the predictive model was built as described above from the a priori known TGCA data using RNA transcription levels from the gene expression panel. The best predictive model had 88% accuracy in cross-validation testing folds and the top 53 genes with highest weighting factor are shown. For example, the PCDHGA4 gene (Protocadherin Gamma Subfamily A, 4) had a weighting factor of −121543.6202 with respect to the RNA expression, with further genes and weighting factors listed below the PCDHGA4 gene. It should be appreciated that multiple, different types of data beyond RNA transcription data were also used to create trained models. The inventor discovered that using the RNA transcription data as training data resulting in the best models (i.e., models having the highest accuracy gain) relative to other trained models that were trained on other types of omic data (e.g., WGS, SNP copy number, proteomics, etc.).

Figure 2:
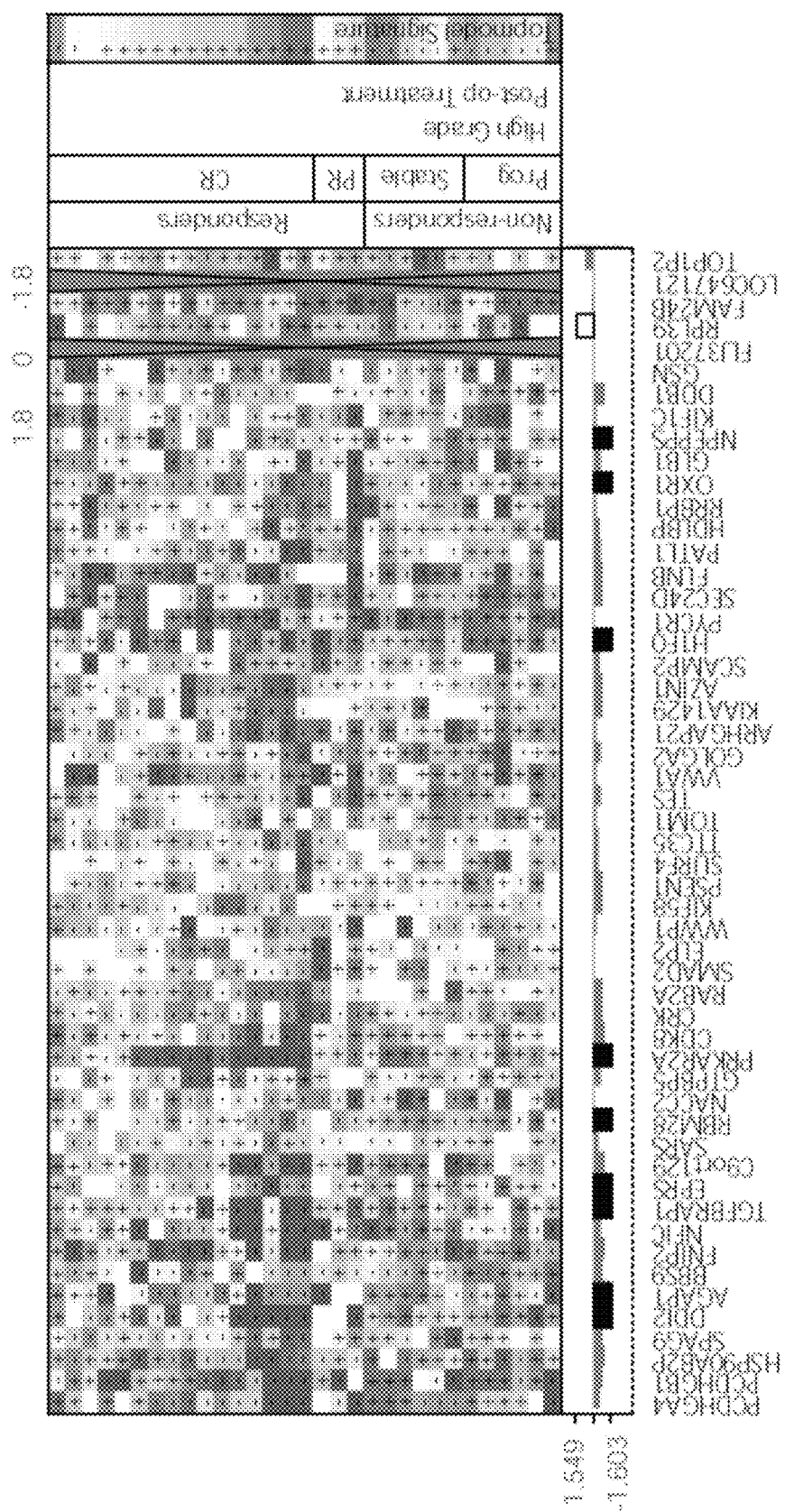
FIG. 2 is an exemplary heat map of RNA transcription values from TCGA high-grade bladder cancer data for responders to drug treatment and non-responders.

FIG. 2 exemplarily illustrates a heat map for the actual patient data where each row in the map corresponds to a single patient, and each column to a specific gene (here, the genes listed in the graph of FIG. 1. As can also be seen from the heat map, the patient data are grouped into responders (categorized in CR: complete response and PR: partial response) and non-responders (categorized in Prog: with disease progression and Stable: without disease progression). Color depth/grayscale value corresponds to measured transcription level and is expressed as color/gray scale value between −1.8 and 1.8. Taken with the weighting factors of FIG. 1, the final predictive score for each patient is the sum of the expression value of FIG. 2 for each gene multiplied by the weighting factor. Any final predictive score above zero (red/grey with + symbol) is indicative of likely treatment response, while a final predictive score below zero (blue/grey with − symbol) is indicative of a likely lack of treatment response. As can be taken from the 'topmodel signature' (final predictive score), only one false positive result was present in the 'Responders' category (top row in Responders category) while the Non-Responders had two false negative results (bottom row in Prog category, bottom row in Stable category).

Moreover, with further reference to the heat map of FIG. 2, it should be appreciated that the statistical significance of each of the RNA transcription data would by itself not be sufficient for an accurate prediction as shown in the bar graph at the bottom portion of the map. Here the bars represent signed t-test values between the results of a responder group and the non-responder group that were corrected for multiple hypothesis testing using Bonferroni correction. As is readily apparent, only a limited set of data exhibited statistically significant differences between responders and non-responders as is shown in the black bars (e.g., DDI2, AGAP1, etc.) and white bar (RPL39). However, when at least some of the individual results are taken together (particularly in combination with the calculated weighting), the predictive power of the model will outperform most, if not all competing other models.

Moreover, it should also be appreciated that using a pathway modeling algorithm (see e.g., WO 2011/139345, WO 2013/062505, WO 2014/059036, and WO 2014/193982) patient data can be used to validate and/or simulate treatment before the patient undergoes actual treatment, and such validation can then be reassessed using the best models for high-grade bladder cancer. For example, highly weighted RNA transcription can be clamped off in silico in the pathway modeling system, and activities are re-inferred, which in effect simulates in silico the anticipated effect of a drug intervention in vivo. The prediction model can then be used to reassess the newly inferred post-intervention data.

In further contemplated aspects of the inventive subject matter it should be recognized that while the example above used RNA transcription data, one or more other (or additional) omics data are also suitable for use in conjunction with the teachings herein. For example, suitable alternative or additional omics data include whole genome differential object data, exome differential object data, SNP data, copy number data, protein expression data, and/or protein activity data. Likewise, meta data associated with the omics data need not be limited to treatment outcome, but may include a large number of alternative patient or care-relevant metrics. For example, contemplated metadata may include treatment cost, likelihood of resistance, likelihood of metastatic disease, 5-year survival, suitability for immunotherapy, patient demographic information, etc.

Similarly, it should be noted that the number of models created is not limiting to the inventive subject matter and that (in general) higher numbers of models are preferred. Such models are preferably based on multiple and distinct machine learning algorithms, and it should be appreciated that all known machine learning algorithms are deemed suitable for use herein. For example, contemplated classifiers include one or more of a linear classifier, an NMF-based classifier, a graphical-based classifier, a tree-based classifier, a Bayesian-based classifier, a rules-based classifier, a net-based classifier, and a kNN classifier. However, especially preferred algorithms will include those that use a classifier selected form the group consisting of NMFpredictor (linear), SVMlight (linear), SVMlight first order polynomial kernel (degree-d polynomial), SVMlight second order polynomial kernel (degree-d polynomial), WEKA SMO (linear), WEKA j48 trees (trees-based), WEKA hyper pipes (distribution-based), WEKA random forests (trees-based), WEKA naive Bayes (probabilistic/bayes), WEKA JRip (rules-based), glmnet lasso (sparse linear), glmnet ridge regression (sparse linear), and glmnet elastic nets (sparse linear). Beyond the above classifiers, additional suitable algorithms include various forms of neural networks (e.g., artificial neural networks, convolution neural networks, etc.), binary decision trees, or other types of learning. Sources for such algorithms are readily available via TensorFlow (see URL www.tensorflow.com), OpenAI (see URL www.openai.com), and Baidu (see URL research.baidu.com/warp-ctc). Thus, the inventor contemplates that at least 5, at least 10, at least 20, at least 50, at least 100, at least 500, at least 1,000, at least 5,000, or at least 10,000 trained models are created. Depending on the number of possible training data sets, the number of validations, and the number of types of algorithms, the number of resulting trained models could even exceed 1,000,000 trained models.

Once the models are created, model quality is assessed and most preferably models are retained that have a prediction power that exceeds random selection. Viewed from a different perspective, models will be assessed on their gain in accuracy. There are numerous manners of assessing accuracy, and the particular choice may depend at least in part on the algorithm used. For example, suitable metrics include an accuracy value, an accuracy gain, a performance metric, or other measure of the corresponding model. Additional example metrics include an area under curve metric, an $R^2$, a p-value metric, a silhouette coefficient, a confusion matrix, or other metric that relates to the nature of the model or its corresponding model template.

For example, accuracy of a model can be derived through use of known data sets and corresponding known clinical outcome data. Thus, for a specific model template a number of evaluation models can be built that are both trained and validated against the input known data sets (e.g., k-fold cross validation). For example, a trained model can be trained based on 80% of the input data. Once the evaluation model has been trained, the remaining 20% of the genomic data can be run through the evaluation model to see if it generates prediction data similar to or closet to the remaining 20% of the known clinical outcome data. The accuracy of the trained evaluation model is then considered to be the ratio of the number of correct predictions to the total number of outcomes.

For example, a RNA transcription data set/clinical outcome data set represents a cohort of 500 patients. The data sets can then be partitioned into one or more groups of evaluation training sets, e.g., containing 400 patient samples. Models are then created based on the 400 patient samples, and the so trained models are validated by executing the model on the remaining 100 patients' transcription data set to generate 100 prediction outcomes. The 100 prediction outcomes are then compared to the actual 100 outcomes from the patient data in the clinical outcome data set. The accuracy of the trained model is the number of correct prediction outcomes relative to the total number of outcomes. If, out of the 100 prediction outcomes, the trained evaluation model generates 85 correct outcomes that match the actual or known clinical outcomes from the patient data, then the accuracy of the trained evaluation model is considered 85%. Alternatively, where the observed outcome (e.g., drug responder) has a frequency of 60% in the meta data of the RNA transcription data set, and where the model generates 85 correct outcomes out of the 100 prediction outcomes, the accuracy gain would be 25% (i.e., 25% above randomly observed results; predicted event occurs at 60%, correct prediction at 85%, accuracy gain is 25%)

Depending on the number of models/accuracy distribution, it should be appreciated that the model used for prediction may be selected as the top model (having highest accuracy gain, or highest accuracy score, etc.), or as being in the top n-tile (tertile, quartile, quintile, etc.), or as being in the top n % of all models (top 5%, top 10%, etc.). Thus suitable models have may have an accuracy gain metric that exceeds all other models.

With respect to the single model, it should be appreciated that the prediction based on the top (or other selected single) model may be based on all of the omics data that were part of the input data (i.e., uses all RNA expression levels used for training the models) or only a fraction of the omics data. For example, where only fractions of the omics data are used for final prediction, the omics data with the highest or minimum absolute predetermined weight (e.g., top quartile of all weights in the single model) in the model will be generally preferred as is shown in the selected features (genes) of FIG. 1. Thus, suitable models will employ at least 5, or at least 10, or at least 20, or at least 50, or at least 100 features in the prediction. Moreover, it should also be appreciated that where features are identified that have substantial statistical significance between the treatment outcomes, these features may be used, preferably in combination, in an gene expression array rather than in a predictive algorithm (e.g., significant features in FIG. 2).

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc. Furthermore, and as used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

What is claimed is:

1. A method of predicting treatment outcome for a patient having high-grade bladder cancer, comprising:
   obtaining a plurality of omics data from the patient, wherein the omics data comprises RNA transcription values;
   generating a plurality of different models using a plurality of respective different machine learning algorithms and a priori omics data;
   determining an accuracy gain metric for each of the plurality of different models;
   using the accuracy gain metric for each of the plurality of different models to select a single model from the plurality of different models for prediction of the treatment outcome of high grade bladder cancer treatment, or selecting a single model from the plurality of different models on the basis of a previously determined accuracy gain metric for prediction of the treatment outcome of high grade bladder cancer treatment;
   calculating, by an analysis engine, a prediction outcome using the single model and the plurality of omics data from the patient;
   wherein the step of calculating comprises a step of selecting features of the single model having minimum absolute predetermined weights, wherein the selected features consist of RNA transcription values for genes consisting of PCDHGA4, PCDHGB1, HSP90AB2P, SPAG9, DDI2, TOP1P2, AGAP1, BBS9, FNIP2, LOC647121, NFIC, TGFBRAP1, EPRS, C9orf129, SARS, RBM28, NACC2, GTPBP5, PRKAR2A, CDK8, FAM24B, CRK, RAB2A, SMAD2, ELP2, WWP1, KIF5B, RPL39, PSEN1, SURF4, TTC35, TOM1, TES, VWA1, GOLGA2, ARHGAP21, FLJ37201, KIAA1429, AZIN1, SCAMP2, H1F0, PYCR1, SEC24D, FLNB, PATL1, HDLBP, RRBP1, OXR1, GLB1, NPEPPS, KIF1C, DDB1, and GSN,
   wherein the accuracy gain metric and the previously determined accuracy gain metric is selected from the group consisting of accuracy gain, accuracy gain distribution, an area under curve metric, an $R^2$, a p-value metric, a silhouette coefficient, and a confusion matrix, wherein the accuracy gain is calculated by comparison of a correct prediction percentage using a validation data set against a percentage of occurrence of a majority classifier, and wherein the accuracy gain metric of the single model is within the upper quartile of all models.

2. The method of claim 1 wherein the single model is selected from among at least 100 models.

3. The method of claim 1 wherein the accuracy gain metric of the single model is within the top 5% of all models.

4. The method of claim 1 wherein the accuracy gain metric of the single model exceeds all other models.

5. The method of claim 1 wherein the prediction outcome is selected from the group consisting of complete response to treatment, partial response to treatment, stable nonresponse to treatment, and progressive non-response to treatment.

6. The method of claim 1 wherein the single model was generated using a machine learning algorithm that uses a classifier selected from the group consisting of NMFpredictor (linear), SVMlight (linear), SVMlight first order polynomial kernel (degree-d polynomial), SVMlight second order polynomial kernel (degree-d polynomial), Waikato Environment for Knowledge Analysis (WEKA) SMO (linear), WEKAj48 trees (trees-based), WEKA hyper pipes (distribution-based), WEKA random forests (trees-based), WEKA naive Bayes (probabilistic/bayes), WEKA JRip (rules-based), glmnet lasso (sparse linear), glmnet ridge regression (sparse linear), and glmnet elastic nets (sparse linear).

7. The method of claim 1 wherein the minimum absolute predetermined weights are within the top quartile of all weights in the single model.

8. The method of claim 1 wherein the RNA transcription values for the genes are calculated with respective factors, and wherein the respective factors are weighted, using absolute values, in the order of PCDHGA4, PCDHGB1, HSP90AB2P, SPAG9, DDI2, TOP1P2, AGAP1, BBS9, FNIP2, LOC647121, NFIC, TGFBRAP1, EPRS, C9orf129, SARS, RBM28, NACC2, GTPBP5, PRKAR2A, CDK8, FAM24B, CRK, RAB2A, SMAD2, ELP2, WWP1, KIF5B, RPL39, PSEN1, SURF4, TTC35, TOM1, TES, VWA1, GOLGA2, ARHGAP21, FLJ37201, KIAA1429, AZIN1, SCAMP2, H1F0, PYCR1, SEC24D, FLNB, PATL1, HDLBP, RRBP1, OXR1, GLB1, NPEPPS, KIF1C, DDB1, and GSN.

9. The method of claim 1 wherein the plurality of RNA transcription data are obtained from poly A RNA.

* * * * *